United States Patent [19]

Sheads

[11] 4,439,368
[45] Mar. 27, 1984

[54] ONE SOLVENT PROCESS FOR PREPARATION OF ESTERS OF 3,5-DIBROMO-4-HYDROXYBENZONITRILE

[75] Inventor: Richard E. Sheads, Durham, N.C.

[73] Assignee: Union Carbide Corporation, Danbury, Conn.

[21] Appl. No.: 426,705

[22] Filed: Sep. 29, 1982

[51] Int. Cl.³ ............................................ C07C 121/75
[52] U.S. Cl. ................................ 260/404; 260/465 D; 260/465 F
[58] Field of Search ................ 260/465 D, 465 F, 404

[56] References Cited

U.S. PATENT DOCUMENTS

| | | | |
|---|---|---|---|
| 3,349,111 | 10/1967 | Luckenbaugh | 260/465 F |
| 3,397,054 | 8/1968 | Hart et al. | 71/105 |
| 3,592,626 | 7/1971 | Heywood et al. | 71/70 |
| 3,671,556 | 6/1972 | Goldstick | 260/404 |
| 4,332,613 | 6/1982 | Esposito | 71/105 |
| 4,349,488 | 9/1982 | Dentel et al. | 260/465 D |

OTHER PUBLICATIONS

Mills et al., *Ind. Eng. Chem. Prod. Res. Develop.*, vol. 12, No. 3, 1973.
Britton et al., Chemical Abstracts, vol. 47, p. 5437, 1953.

*Primary Examiner*—Dolph H. Torrence
*Attorney, Agent, or Firm*—J. A. Shedden

[57] ABSTRACT

Esters of 3,5-dibromo-4-hydroxybenzonitrile can be prepared in high yields from 4-cyanophenol in a single solvent. In this manner, the 3,5-dibromo-4-hydroxybenzonitrile intermediate need not be isolated, and therefore the bromination and esterification reactions can be performed in one reactor. Preferably, the bromination is accomplished with bromine chloride in the presence of 1,1,2-trichloroethane followed by esterification with an acid chloride in the same solvent.

12 Claims, No Drawings

ONE SOLVENT PROCESS FOR PREPARATION OF ESTERS OF 3,5-DIBROMO-4-HYDROXYBENZONITRILE

FIELD OF THE INVENTION

This invention relates to a novel method of preparing esters of 3,5-dibromo-4-hydroxybenzonitrile.

BACKGROUND OF THE INVENTION

Certain esters of the 3,5-dichloro-; 3,5-dibromo-; and 3,5-diiodo-4-hydroxybenzonitriles, also known respectively as chloroxynil, bromoxynil and ioxynil are extensively used as broadleaf weed herbicides, particularly in crop-growing areas.

Examples of such esters are those formed from the 3,5-dichloro-, 3,5-dibromo-, or 3,5-diiodo-4-hydroxybenzonitriles and unsubstituted or halogenated aliphatic, cycloaliphatic or aromatic acids, such as trichloroacetic, propionic, 2,2-dichloropropionic, n-butanoic, n-octanoic, 2-ethylhexanoic, cyclohexylcarboxylic, benzoic and benzenesulfonic acids.

Three syntheses of these herbicides from the dihalohydroxybenzonitriles have been described in the prior art.

U.S. Pat. No. 3,592,626 (Heywood et al) details two methods. According to one, the 3,5-dihalo-4-hydroxybenzonitrile is reacted with an organic anhydride in the presence of a condensing agent, such as concentrated sulfuric acid or a sodium or potassium salt of the corresponding organic acid. According to the other method, the benzonitrile derivative is reacted with an acid halide, e.g., the chloride, in the presence of a tertiary base, e.g., pyridine, or in the presence of a quaternary ammonium salt, e.g. tetralkylammonium chloride.

Both of these methods have disadvantages and shortcomings.

In the anhydride method, only one-half of the acid equivalent of the anhydride is reacted with the hydroxy-benzonitrile, the other half is converted into free acid which must be removed from the reaction mixture and is essentially a waste product. Also, the removal of the condensing agent, sulfuric acid or alkali salt of the organic acid, needs additional processing and causes extra expenses when the ester of the benzonitrile is needed in a purified form.

The use of tertiary bases, such as pyridine, usually in excess, in the second method mentioned is expensive and complicates the synthesis process for the following reason. Most of the base has to be recovered for reuse, necessitating an appropriate separation step such as distillation. The portion of the base which served as acceptor for the hydrogen chloride formed requires other processing steps as it has to be separated from the ester product.

The variant of the acid chloride method carried out in the presence of quaternary salts has the disadvantage of employing these rather costly salts. Their direct recovery for reuse is expensive, if not impossible and even the separation of these salts from the product ester involves such steps as addition of solvent, neutralization and crystallization.

U.S. Pat. No. 3,671,556 (Goldstick) discloses a third method for the preparation of esters of 3,5-dihalo-4-hydroxybenzonitriles. It is taught that the esters can be formed by the direct reaction of the hydroxybenzonitrile derivatives with the appropriate acid halides, if the dry, solid hydroxybenzonitrile is gradually added to a slight excess of the liquid acid halide, e.g. capryloyl chloride, kept at a temperature above 120° C. The reaction need not be carried out in the presence of any base, acid acceptor, catalyst or condensing agent, however, it is suggested that in the case where the acid chloride is unusually viscous or high-melting, a solvent can be used.

All of the above processes, of course, anticipate preparing the esters from a previously isolated dihalohydroxybenzonitrile reactant.

With regard to the preparation of these dihalohydroxybenzonitrile reactants, E. Muller et al, Chem. Ber. 92, 2278(1959) teaches that p-hydroxy-benzonitrile should be dissolved in methanol and glacial acetic acid and then treated with bromine. The product is then poured into an aqueous methanolic solution of $NaHSO_3$.

Luckenbaugh (U.S. Pat. No. 3,349,111) discloses that 3,5-dibromo-4-hydroxybenzonitrile can be prepared by reacting an aqueous suspension of p-hydroxybenzonitrile with aqueous alkali metal hydroxide or aqueous alkali metal carbonate; reacting the mixture with bromine; further reacting this mixture with chlorine; then acidifying the mixture and finally filtering to obtain the product. An alternative process eliminates the base.

In none of the prior art processes for preparing dihalohydroxybenzonitriles, can the product be esterified in situ, i.e., in every prior art process, the dihalohydroxybenzonitrile product must be isolated from the product reaction mixture before esterification can be realized because the prior art bromination solvent/reaction media are incompatable with the prior art esterification solvent/reaction media.

SUMMARY OF THE INVENTION

In accordance with the present invention, it has been discovered that esters of 3,5-dibromo-4-hydroxybenzonitrile can be prepared in high yields from 4-cyanophenol in a single solvent.

The bromination can be accomplished by reacting the 4-cyanophenol with (1) bromine; or (2) bromine and chlorine either sequentially or at the same time; or (3) preferably preformed bromine chloride in the presence of a halogenated aliphatic, preferably a halogenated $C_2$ to $C_4$ alkane followed by esterification of the 3,5-dibromo-4-hydroxybenzonitrile with an aliphatic, cycloaliphatic or aromatic acid halide without isolating the intermediate from the reaction medium.

The overall reaction can be illustrated by the following:

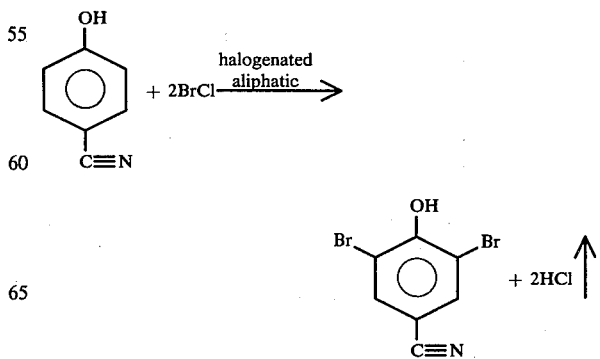

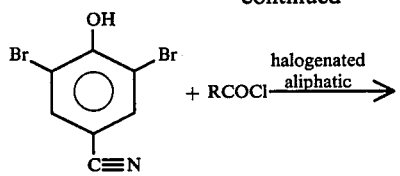

-continued

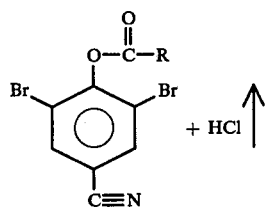

The organic groups designated by the symbol R are intended to include all of the usual organic acid moieties, i.e., aliphatic, cycloaliphatic, or aromatic which are available as the corresponding acid chloride.

DETAILED DESCRIPTION OF THE INVENTION

The invention relates to the discovery that 4-cyanophenol can be brominated using preformed bromine chloride to 3,5-dibromo-4-hydroxy-benzonitrile which in turn can be esterified with an aliphatic, cycloaliphatic or aromatic acid halide; both reactions taking place sequentially in a single solvent medium, i.e., a halogenated aliphatic.

A detailed discussion regarding the properties of preformed bromine chloride can be found in "Bromine Chloride: An Alternative to Bromine", *Ind. Eng. Chem. Prod. Res. Develop.* Vol 12 No. 3, 1973 by Mills and Schneider.

The preferred acid halides are the chlorides, particularly the aliphatic acids, both straight and branched chain, having from 3 to 18 carbon atoms and most preferably from 4 to 12 carbon atoms. Substituted aliphatic acid groups wherein one or more of the hydrogen atoms has been replaced by a functional group such as halo, are also included. Suitable aromatic acids are the aralkanoic acids such as benzoic acid and the same where the aromatic moiety is substituted with functional groups such as $C_1$ to $C_5$ alkyl, halo, sulfonyl, trifluoromethyl, nitro, and the like.

The preferred acid chlorides used in the process of this invention are those having a boiling point above about 100° C. though lower boiling acid chlorides can be used in which case the reaction is suitably carried out at an elevated pressure sufficient to attain a reaction temperature of about 100° C. or higher while maintaining the acid chloride in the liquid phase.

The halogenated aliphatic solvents useful in the single solvent process of this invention must, of course, be inert to the preformed bromine chloride and the selected acid halide. Furthermore, the solvent must provide solubility at reflux for both the 4-cyanophenol and the halogenated phenol, i.e., bromoxynil. Preferably, the halogenated aliphatics are halogenated $C_2$ to $C_4$ alkanes with boiling points greater than about 100° C. The most preferred halogenated aliphatic solvents are the 1,1,1- and 1,1,2-trichloroethanes; and the 1,1,1,2- and 1,1,2,2-tetrachloroethanes.

The bromination and esterification reaction mixtures are refluxed until the respective reactions are completed at temperatures in excess of 100° C., usually in excess of 110° C.

Atmospheric pressure is usually employed in effecting the reactions according to the process of the instant invention. However, pressures both above and below atmospheric pressure can also be employed whenever it is desirable to do so.

The following examples are set forth for purposes of illustration so that those skilled in the art may better understand the invention, and it should be understood that they are not to be construed as limiting this invention in any manner.

EXAMPLE 1

Synthesis of octanoate ester of 3,5-dibromo-4-hydroxybenzonitrile 65 grams (0.546 mole) of 4-cyanophenol was slurried in 200 ml of 1,1,2-trichloroethane with mechanical stirring and 60 ml (10% excess) of bromine chloride added dropwise at a rate of 1 mol/min. After complete addition of the bromine chloride, the reaction mixture is refluxed for 2 hours to complete the reaction. To the refluxing solution is added slowly 100 ml (7% excess) of octanoyl chloride. The solution is refluxed 6 hours after addition to acid chloride is completed. The solution is then cooled and 10 ml of methanol is added to react with excess acid chloride and the solvent is then removed by distillation under vacuum. The residue which solidifies on cooling is obtained in 90% yield (198 g), mp 38°–42° C. The purity of product was shown by gc profile to be 96.5%

EXAMPLE 2

Synthesis of butyrate ester of 3,5-dibromo-4-hydroxybenzonitrile

The procedure is the same as that used in Example 1. 61 mol (7% excess) of butyryl chloride is used in place of the octanoyl chloride. A total of 190 g of product are obtained in 98% yield, mp 70°–75° C. The purity of product was shown by gc profile to be 97.7%.

I claim:

1. A method of preparing esters of 3,5-dibromo-4-hydroxybenzonitrile from 4-cyanophenol which comprises:
    (a) reacting said 4-cyanophenol with a reactant(s) selected from the group consisting of bromine; bromine and chlorine; and preformed bromine chloride;
    (b) sequentially reacting the 3,5-dibromo-4-hydroxybenzonitrile intermediate so formed with an acid halide selected from the group consisting of an aliphatic, cycloaliphatic and aromatic acid halide; and
    (c) conducting both of the above process steps in a single, halogenated alkane reaction medium.

2. A method of preparing esters of 3,5-dibromo-4-hydroxybenzonitrile from 4-cyanophenol which comprises:
    (a) reacting said 4-cyanophenol with preformed bromine chloride;
    (b) sequentially reacting the 3,5-dibromo-4-hydroxybenzonitrile intermediate so formed with an acid halide selected from the group consisting of an aliphatic, cycloaliphatic and aromatic acid halide; and
    (c) conducting both of the above process steps in a single, halogenated alkane reaction medium.

3. A method of preparing esters of 3,5-dibromo-4-hydroxybenzonitrile from 4-cyanophenol which comprises:
(a) reacting said 4-cyanophenol with preformed bromine chloride;
(b) sequentially reacting the 3,5-dibromo-4-hydroxybenzonitrile intermediate so formed with an acid halide selected from the group consisting of an aliphatic, cycloaliphatic and aromatic acid halide; and
(c) conducting both of the above process steps in a halogenated $C_2$ to $C_4$ alkane.

4. The method of claim 3 wherein said single halogenated $C_2$ to $C_4$ alkane has a boiling point in excess of 100° C.

5. The method of claim 4 wherein said halogenated $C_2$ to $C_4$ alkane is selected from the group consisting of 1,1,1-trichloroethane; 1,1,2-trichloroethane, 1,1,1,2-tetrachloroethane; and 1,1,2,2-tetrachloroethane.

6. The method of claim 4 wherein said halogenated $C_2$ to $C_4$ alkane is 1,1,2-trichloroethane.

7. A method of preparing esters of 3,5-dibromo-4-hydroxybenzonitrile from 4-cyanophenol which comprises:
(a) reacting said 4-cyanophenol with preformed bromine chloride;
(b) sequentially reacting the 3,5-dibromo-4-hydroxybenzonitrile intermediate so formed with an aliphatic acid halide; and
(c) conducting both of the above process steps in a single, halogenated alkane reaction medium.

8. The method of claim 7 wherein the aliphatic acid halide is a halide of an alkenoic acid either straight or branched having from 3 to 18 carbon atoms, unsubstituted or substituted by one or more halogen groups.

9. The method of claim 8 wherein the aliphatic acid halide is butyryl chloride.

10. The method of claim 8 wherein the aliphatic acid halide is octanoyl chloride.

11. A method of preparing esters of 3,5-dibromo-4-hydroxybenzonitrile from 4-cyanophenol which comprises:
(a) reacting said 4-cyanophenol with preformed bromine chloride;
(b) sequentially reacting the 3,5-dibromo-4-hydroxybenzonitrile intermediate so formed with an aromatic acid halide; and
(c) conducting both the above process steps in a single, halogenated alkane reaction medium.

12. The method of claim 11 wherein the aromatic acid halide is a halide of unsubstituted benzoic acid or benzoic acid substituted by one or more functional groups selected from the group consisting of $C_1$ to $C_5$ alkyl, halo, sulfonyl, trifluoromethyl, and nitro.

* * * * *